United States Patent [19]

Bitrolf

[11] Patent Number: 5,064,424

[45] Date of Patent: Nov. 12, 1991

[54] ELECTRO-SURGICAL INSTRUMENT

[75] Inventor: Ehrenfried Bitrolf, Knittlingen-Kleinvillars, Fed. Rep. of Germany

[73] Assignee: Richard Wolf GmbH, Knittlingen, Fed. Rep. of Germany

[21] Appl. No.: 488,902

[22] Filed: Mar. 6, 1990

[30] Foreign Application Priority Data

May 18, 1989 [DE] Fed. Rep. of Germany ....... 3916161

[51] Int. Cl.⁵ .............................................. A61B 17/39
[52] U.S. Cl. ......................................... 606/46; 606/49
[58] Field of Search .............................. 606/45, 46, 49

[56] References Cited

U.S. PATENT DOCUMENTS

| | | | |
|---|---|---|---|
| 1,932,258 | 10/1933 | Wappler | 606/45 |
| 2,447,169 | 8/1948 | Sousa | 606/45 |
| 3,532,095 | 6/1968 | Miller et al. | 606/45 |
| 4,362,160 | 12/1982 | Hittebrandt | 606/46 |

FOREIGN PATENT DOCUMENTS 1835081 7/1961 Fed. Rep. of Germany .
8423501 12/1984 Fed. Rep. of Germany .

Primary Examiner—Lee S. Cohen
Attorney, Agent, or Firm—Panitch, Schwarze, Jacobs & Nadel

[57] ABSTRACT

The invention relates to an electro-surgical instrument having a probe stem whose distal end is provided with an electrode connectable to an HF current source. To enable the electrode to be used both for coagulation and for resection accompanied by coagulation, the electrode has a part-spherical portion and an annular portion. This annular portion is arranged to project up at an angle from a plane face of the part-spherical portion.

5 Claims, 1 Drawing Sheet

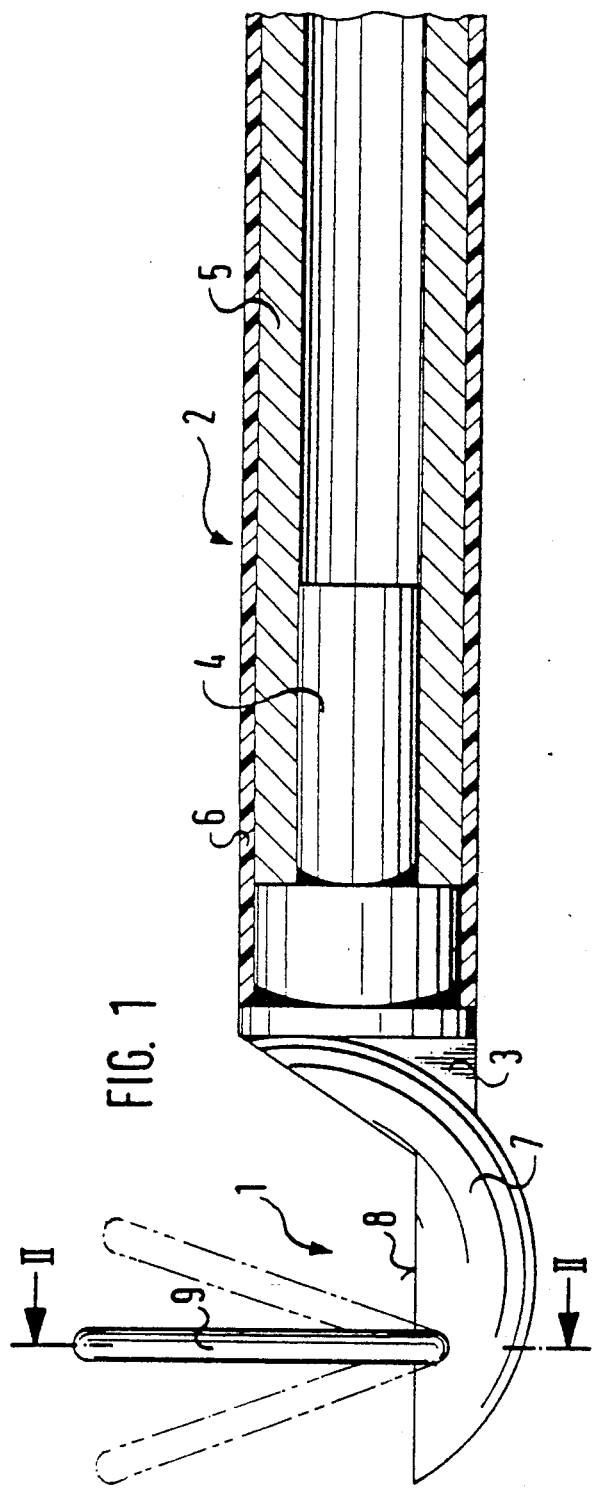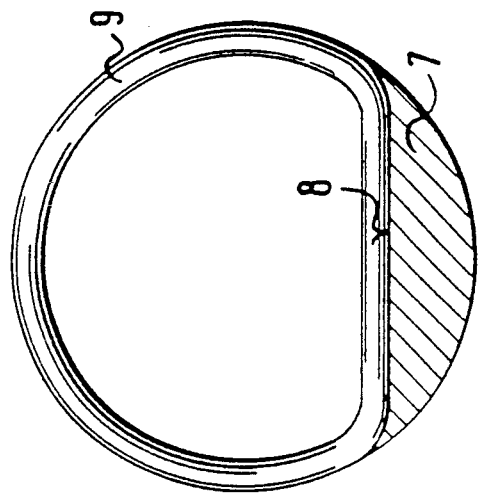

ELECTRO-SURGICAL INSTRUMENT

BACKGROUND OF THE INVENTION

1. Field of the Invention

This invention relates to an electro-surgical instrument of the type having a probe stem which stem has an electrode at its distal end connectable to an HF current source.

2. Description of the Prior Art

Instruments of the type referred to above are well known in the medical field. They are used for so-called electro-coagulation, a technique in which, due to a high field density, the action of an HF current causes overheating in tissue cells which come into contact with the electrode. This overheating causes colloidal matter to precipitate out of the colloidal solution containing it.

An individual electro-surgical instrument, or rather the electrode which comes directly into contact with the biological tissue, has a three-dimensional shape selected to suit its intended purpose. Thus U.S. Pat. No. 3,532,095 and DE-GM 8,423,501 for example disclose electro-surgical instruments which have a spherical electrode at the distal end of the stem, which electrode is arranged in such a way as to be easily exchangeable.

DE-AS 2,324,658 discloses an HF probe for coagulating biological body tissue which, to avoid having a ground electrode of large area, is in the form of a bipolar electrode, having a first, annular electrode and, spaced therefrom, a second electrode of hemispherical shape which forms the distal end of the HF probe.

Another prior art device can be found in DE-OS 2,941,060, which discloses a resection device in which the electrode, through which an HF current flows, is in the form of a loop. The loop can be placed around pieces of tissue which project from bodily surface, such as polyps or the like, so that the piece of tissue can be resected while the area of the cut is coagulated at the same time. The resection loop is longitudinally displaceable within a tubular stem, whereby the width of the resection loop can be varied.

Resection loops are also known from DE-PS 2525982. This document shows how a resection loop can be used for prostate resection and allows tissue to be cut away in strips, that is to say it allows tissue resection whilst coagulating the cut face at the same time.

The structural configuration of the electrodes in probe and loop form which are used for tissue coagulation and resection is matched chiefly to their particular intended purpose, thus making them usable only to a small degree, if at all, for any other purpose.

If, in an endoscopic operation in the rectum for example, there is a need not only for coagulation but also for resection, then in accordance with the state of the art it is necessary to have at least an instrument with interchangeable HF electrodes, or else two separate instruments with specially shaped HF electrodes.

Hence, the disadvantages of known designs lie on the one hand in the fact that HF electrodes which can be secured to the instrument but are exchangeable may be lost in the rectum, and on the other hand; that there is inevitably an additional stress on the patient due to the fact that, both with instruments designed as above and when using a number of specially shaped instruments the time taken by the endoscopic operation is longer because of the time needed to change the instruments.

An object of the invention is therefore to avoid the disadvantages from which these known designs suffer.

SUMMARY OF THE INVENTION

According to the invention an electro-surgical instrument comprises a probe stem having a distal end, and; an electrode connectable to an HF source and situated at the distal end of the probe stem; wherein the electrode comprises a part-spherical portion, the part-spherical portion having a substantially planar face, and an annular portion upstanding from said planar face of the part-spherical portion.

The annular portion may usefully be so arranged that its plane extends substantially perpendicularly to the longitudinal axis of the probe stem.

The principal advantage of an electrode formed in this way lies in its combined usability both for coagulation and for resection accompanied by coagulation of the face of the cut.

In another embodiment of the invention, the electrode may be shaped in such a way that a cross-sectional surface imagined to extend in the plane of the annular portion and through the part-spherical portion is circular in outline, though the plane of the annular portion may also extend in an inclined position relative to the longitudinal axis of the stem. With regard to safety in use, it is advantageous for the annular portion to be non-detachably connected to the part-spherical portion.

BRIEF DESCRIPTION OF THE DRAWINGS

FIG. 1 is a side elevation with the probe stem shown in partial longitudinal section, and FIG. 2 is a sectional view on line II—II in FIG. 1.

DETAILED DESCRIPTION

Referring to FIG. 1, a combination electrode 1 comprises a probe stem 2 into whose distal end an electrode 3 is inserted by means of a stepped extension 4 on the electrode. The extension can be connected to one pole of an HF generator, via a conductor (not shown). The electrical connection may also be made via a stem 5, which may equally well be in the form of a flexible metal coil. To avoid any unintentional transmission of current, the conductor and the stem 5 are provided with external insulation 6.

The electrode 3, which would otherwise be spherical, is in the shape of a part-spherical portion 7 by virtue of a sectioning face 8 extending parallel to the longitudinal axis of the probe stem 2. Thus, the curved outer surface of the part-spherical portion 7 faces in a direction substantially transverse to the longitudinal axis of the probe stem 2.

An annular portion 9 projects from the sectioning face 8 of the part-spherical portion 7, in the region of the latter's distal end. The annular portion 9 is non-detachably connected to the part-spherical portion 7, with the plane of the annular portion extending perpendicularly to the longitudinal axis of the probe stem 2 and to the sectioning face 8 in this embodiment. As FIG. 2. shows, the annular portion 9 is shaped in such a way as to define with the part-spherical portion 7 a circular cross-sectional surface.

Irrespective of the three-dimensional shape shown for the annular portion 9 in FIG. 2, both its geometry and its dimensions may be freely selected. Furthermore, it is also conceivable for the angle between the sectioning face 8 and the annular portion 9 to be varied in order to make manipulation easier for the user or to allow special operations to be performed deep in the rectum. That is, annular portion 9 may be inclined relative to the longitudinal axis of the probe stem 2, as shown for example by the tow positions of the annular portion shown in phantom in FIG. 1.

I claim:

1. An electro-surgical instrument comprising:
   a probe stem having a longitudinal axis and a distal end, and:
   an electrode connectable to an HF source and situated at the distal end of the probe stem;
   wherein the electrode comprises a part-spherical portion, the part-spherical portion having a substantially planar face, and an annular portion upstanding from said planar face of the part-spherical portion.

2. An electro-surgical instrument according to claim 1, wherein the annular portion lies in a plane extending substantially perpendicularly to the longitudinal axis of the probe stem.

3. An electro-surgical instrument according to claim 1, wherein the electrode is shaped such that a cross-section in the plane in which the annular portion lies, taken through the annular portion and through the part-spherical portion, is of substantially circular outline.

4. An electro-surgical instrument according to claim 1, wherein the annular portion lies in a plane which is inclined relative to the longitudinal axis of the probe stem.

5. An electro-surgical instrument according to claim 1, wherein the annular portion is non-detachably connected to the part-spherical portion.

* * * * *